US011953419B2

(12) United States Patent
Hwang et al.

(10) Patent No.: US 11,953,419 B2
(45) Date of Patent: Apr. 9, 2024

(54) APPARATUS FOR MONITORING BIOAEROSOLS USING MACHINE LEARNING AND METHOD THEREOF

(71) Applicant: INDUSTRY-ACADEMIC COOPERATION FOUNDATION, YONSEI UNIVERSITY, Seoul (KR)

(72) Inventors: Jung Ho Hwang, Seoul (KR); Sang Gwon An, Uijeongbu-si (KR); Hyeong Rae Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 685 days.

(21) Appl. No.: 17/182,731

(22) Filed: Feb. 23, 2021

(65) Prior Publication Data

US 2022/0268686 A1    Aug. 25, 2022

(51) Int. Cl.
| | | |
|---|---|---|
| *G01N 15/1404* | (2024.01) | |
| *B01D 47/00* | (2006.01) | |
| *B03C 3/41* | (2006.01) | |
| *B03C 3/47* | (2006.01) | |
| *C12Q 1/04* | (2006.01) | |
| *G01N 30/72* | (2006.01) | |

(Continued)

(52) U.S. Cl.
CPC ......... *G01N 15/1404* (2013.01); *B01D 47/00* (2013.01); *B03C 3/41* (2013.01); *B03C 3/47* (2013.01); *C12Q 1/04* (2013.01); *G01N 30/7266* (2013.01); *G06N 20/00* (2019.01); *G01N 2015/1481* (2013.01)

(58) Field of Classification Search
CPC ............... G01N 15/1404; G01N 15/06; G01N 15/1429; G01N 15/1433; G01N 15/01; G01N 30/7266; G01N 2015/1481; G01N 2015/0681; G01N 2015/0687; B01D 47/00; B03C 3/41; B03C 3/47; B03C 3/017; B03C 3/53; B03C 2201/06; C12Q 1/04; G06N 20/00
USPC ........................................................ 250/288
See application file for complete search history.

(56) References Cited

U.S. PATENT DOCUMENTS

2022/0266240 A1*  8/2022  Hwang ................ G01N 21/783

FOREIGN PATENT DOCUMENTS

| JP | 4797652 B2 | 10/2011 |
|---|---|---|
| JP | 5059740 B2 | 10/2012 |
| JP | 2015-210209 A | 11/2015 |

(Continued)

OTHER PUBLICATIONS

Korean Notice of Allowance 10-2019-0125371 dated Jan. 4, 2021.

*Primary Examiner* — Kiet T Nguyen
(74) *Attorney, Agent, or Firm* — Sughrue Mion, PLLC (57) ABSTRACT

Disclosed is an apparatus for monitoring bioaerosols, including a capturer configured to capture bioaerosol particles in air in a capture solution; a particle sprayer configured to electro-spray the capture solution in a form of droplets such that the particles are included in at least some of the sprayed droplets; and an analyzer configured to analyze the particles, sprayed through the particle sprayer, by machine learning. In accordance with such a configuration, the droplets containing a certain amount of the particles can be continuously analyzed in real time by machine learning, thereby contributing to the improvement of monitoring efficiency for a specific bioaerosol genus.

19 Claims, 5 Drawing Sheets

(51) Int. Cl.
*G06N 20/00* (2019.01)
*G01N 15/14* (2006.01)

(56) References Cited

FOREIGN PATENT DOCUMENTS

| | | |
|---|---|---|
| JP | 2018-132301 A | 8/2018 |
| KR | 10-2010-0002010 A | 1/2010 |
| KR | 10-2015-0051456 A | 5/2015 |
| KR | 10-1568333 B1 | 11/2015 |
| KR | 10-2016-0111140 A | 9/2016 |
| KR | 10-2017-0012260 A | 2/2017 |
| KR | 10-1779039 B1 | 9/2017 |
| KR | 10-2017-0112404 A | 10/2017 |
| KR | 10-2018-0004898 A | 1/2018 |
| KR | 10-2018-0103546 A | 9/2018 |
| KR | 10-1912521 B1 | 10/2018 |
| KR | 10-2019-0030146 A | 3/2019 |
| KR | 10-2019-0043135 A | 4/2019 |

\* cited by examiner

APPARATUS FOR MONITORING BIOAEROSOLS USING MACHINE LEARNING AND METHOD THEREOF

BACKGROUND OF THE DISCLOSURE

Field of the Disclosure

The present disclosure relates to an apparatus for monitoring bioaerosols and a method thereof, and more particularly, to an apparatus for monitoring bioaerosols using machine learning to continuously monitor the concentration of a specific bioaerosol genus in air in real time, and a method thereof.

Description of the Related Art

As general methods of measuring microorganisms, i.e., bioaerosols, suspended in air, a culture method of allowing biological particles suspended in a sample gas to be captured to a solid or liquid surface suitable for proliferation and culturing the same in an appropriate temperature and humidity environment for a certain period to measure the captured microorganisms; and a staining method of staining captured microorganisms and measuring the same using a fluorescence microscope are mainly used.

Recently, a series of processes required for ATP scavenging, ATP extraction, and light emission amount measurement can be shortened to about 30 minutes by an ATP bioluminescence method of using the principle that adenosine triphosphate (ATP) and luciferin/luciferase react to emit light, which allows rapid measurement. For reference, a bioaerosol measurement method using such an ATP bioluminescence method is suitable for determining the total concentration of bioaerosols in air.

In recent years, there is high interest in how much of a specific bioaerosol genus, which is highly harmful to the human body, among bioaerosols exists in air. However, polymerase chain reaction (PCR) mainly used to detect the concentration of a specific bioaerosol genus in air requires a long detection time of 2 to 3 hours, and a preparation process of a sample to be used in a PCR equipment is complex.

Accordingly, various research into improving the monitoring efficiency of a specific bioaerosol genus in air is continuously being conducted in recent years.

RELATED ART DOCUMENTS

Patent Documents

Non-Patent Documents

Korean Patent No. 10-1912521
Japanese Patent No. 4797652

SUMMARY OF THE DISCLOSURE

Therefore, the present disclosure has been made in view of the above problems, and it is an object of the present disclosure to provide an apparatus for monitoring bioaerosols using machine learning to continuously monitor a specific bioaerosol genus among bioaerosol particles in air in real time.

It is another object of the present disclosure to provide a method of monitoring bioaerosols using machine learning to continuously monitor, by genus, bioaerosol particles in air in real time.

In accordance with an aspect of the present disclosure, the above and other objects can be accomplished by the provision of an apparatus for monitoring bioaerosols, including: a capturer configured to capture bioaerosol particles in air in a capture solution; a particle sprayer configured to electro-spray the capture solution in a form of droplets such that the particles are included in a certain amount in at least some of the droplets; and an analyzer configured to analyze the particles, sprayed through the particle sprayer, by machine learning.

In addition, the particle sprayer may include a particle discharge body provided with a particle inlet into which the capture solution capturing the particles therein is introduced; and a particle outlet which extends in a longitudinal direction from the particle inlet and serves to discharge the droplets; a particle discharge cone with a Taylor cone shape provided between the particle inlet and the particle outlet and configured to electro-spray the capture solution such that the droplets including a certain amount of the particles are individually discharged; a particle controller configured to apply an electrostatic force greater than surface tension of the capture solution to the particle discharge cone so as to control opening and closing of the particle discharge cone; and an oil supplier configured to supply an oil to the droplets discharged from the particle discharge cone so as to maintain a state of the droplets, wherein the droplets are electro-sprayed to a constant position at a constant speed.

In addition, the apparatus may further include a reagent supplier configured to supply a reagent, capable of reacting with the particles, toward the droplets discharged from the particle sprayer; and a reactor in which the particles and the reagent are mixed and reacted, wherein the analyzer analyzes images, obtained by observing the particles reacted with the reagent discharged from the reactor, by machine learning.

In addition, the reagent supplier may include a second discharge body provided with a reagent inlet into which the reagent is introduced; and a reagent outlet formed to extend in a longitudinal direction from the reagent inlet and discharge the reagent; a reagent discharge cone with a Taylor cone shape provided between the reagent inlet and the reagent outlet and configured to electro-spray the reagent; and a reagent controller serving to control such that an electrostatic force greater than surface tension of the reagent is applied to the reagent discharge cone so as to control opening and closing of the reagent discharge cone.

In addition, the reagent discharge cone may spray the reagent in a state of droplets, and supply an oil to the reagent in a droplet state discharged from the reagent discharge cone to maintain the droplet state.

In addition, an open area of the particle discharge cone may be controlled by the particle controller such that the droplets contain a certain amount of the particles with a size of less than 1 μm.

In addition, the capture solution and the oil may be supplied in a flow rate ratio of 5 μL/hour:400 μL/hour to the particle discharge body, a voltage of 5500 to 6500V may be applied to a first positive electrode application body and first negative electrode application body that respectively apply a positive electrode and a negative electrode, the particle discharge cone being disposed between the first positive electrode application body and the first negative electrode application body first, and the oil may contain 3 to 7% of a surfactant.

In addition, an open area of the reagent discharge cone may be controlled to a size of less than 1 μm by the reagent controller.

In addition, the reactor may be provided with a reaction path bent a plurality of times, wherein the droplets discharged from the particle sprayer and the reagent discharged from the reagent supplier are mixed in the reaction path.

In addition, the reagent may include a fluorescent liquid capable of reacting with microorganisms to stain the particles, and the analyzer may analyze images, obtained by observing the stained particles using a photosensor or a fluorescence microscope, by machine learning.

In accordance with another aspect of the present disclosure, there is provided a method of monitoring bioaerosols, the method including: a particle spray process of electro-spraying a capture solution, in which bioaerosol particles are captured, in the form of particle droplets including a certain amount of the particles; and a machine learning analysis process of observing the particles droplets to analyze the bioaerosols by genus through machine learning.

In addition, the method may further include a reagent reaction process of electro-spraying a reagent, capable of reacting with the particles, in a form of reagent droplets to react with the particles droplets, wherein the machine learning analysis process including measuring and analyzing the particles droplets capable of reacting with the reagent.

In addition, the reagent reaction process may include: a reagent spray process of spraying the reagent in the form of reagent droplets; and a reaction process of mixing and reacting the particles droplets with the reagent droplets, wherein the particle spray process and the reagent spray process are simultaneously performed or the reagent spray process is performed before or after the particle spray process.

In addition, the particle spray process may include a process of introducing the capture solution into a particle discharge body; a process of electro-spraying the particles droplets including a certain amount of the particles from a particle discharge cone with a Taylor cone shape, provided inside the particle discharge body, to a constant position at a constant speed; and a first oil supply process of supplying an oil to the particles droplets, wherein an electrostatic force greater than surface tension of the capture solution is applied to the particle discharge cone so that opening of the particle discharge cone is controlled to spray the particles droplets.

In addition, an opening area of the particle discharge cone may be controlled such that the particles having a size of less than 1 µm are included in a certain amount in the particles droplets.

In addition, the capture solution may be continuously supplied in the particle spray process such that the machine learning analysis process is continuously performed in real time.

In accordance with yet another aspect of the present disclosure, there is provided a method of monitoring bioaerosols, the method including: a learning process of previously learning bioaerosols; and an analysis process of analyzing a capture solution, in which continuously introduced bioaerosols are captured, by machine learning, wherein the analysis process includes monitoring the concentration of the bioaerosols by genus through the machine learning.

In addition, the capture solution may be electro-sprayed in a form of droplets such that the bioaerosol particles are included in a certain amount and react with a reagent, and the analysis process may include measuring and analyzing the particles droplets reacted with the reagent.

In addition, a plurality of capture solutions may be provided to respectively include different bioaerosol genera, and the analysis process may include respectively analyzing the plurality of capture solutions so as to analyze the bioaerosols by genus through machine learning.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, a preferred embodiment of the present disclosure is described with reference to the accompanying drawings. However, it should be understood that the spirit and scope of the present disclosure are not limited to the embodiments and can be modified by addition, modification, or deletion of elements constituting the embodiments and such additions, modifications, and deletions are also within the spirit and scope of the present disclosure.

Figure 1:
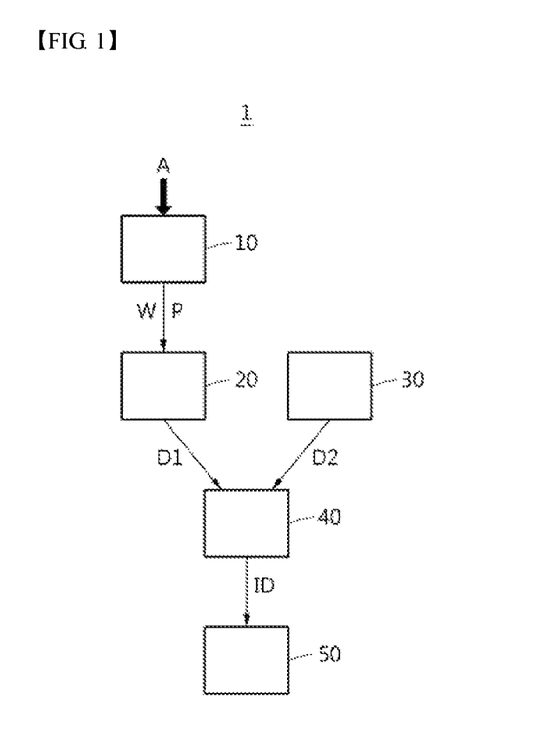
FIG. 1 is a block diagram schematically illustrating an apparatus for monitoring bioaerosols according to a preferred embodiment of the present disclosure.

Referring to FIG. 1, an apparatus 1 for monitoring bioaerosols according to a preferred embodiment of the present disclosure includes a capturer 10, a particle sprayer 20, a reagent supplier 30, a reactor 40 and an analyzer 50.

By the capturer 10, microbial particles, i.e., bioaerosol particles P, in air A are captured in a capture solution W. In the present embodiment, the microbial particles P, such as bacteria and viruses having a relatively small size, among the microbial particles (P) in air A are exemplified as being captured in the capturer 10.

For reference, in the present disclosure, the particles P may be classified by size through a classification means (not shown) before the air A is introduced into the capturer 10. Here, the classification means (not shown) may use a virtual impactor provided with microchannels for classifying the particles P by size, but this is not the gist of the present disclosure and thus detailed illustration and description thereof are omitted. In addition, a modified example in which the classification means (not shown) is not provided and the air A is directly introduced into the capturer 10 to capture the particles P in air A is also possible.

Figure 2:
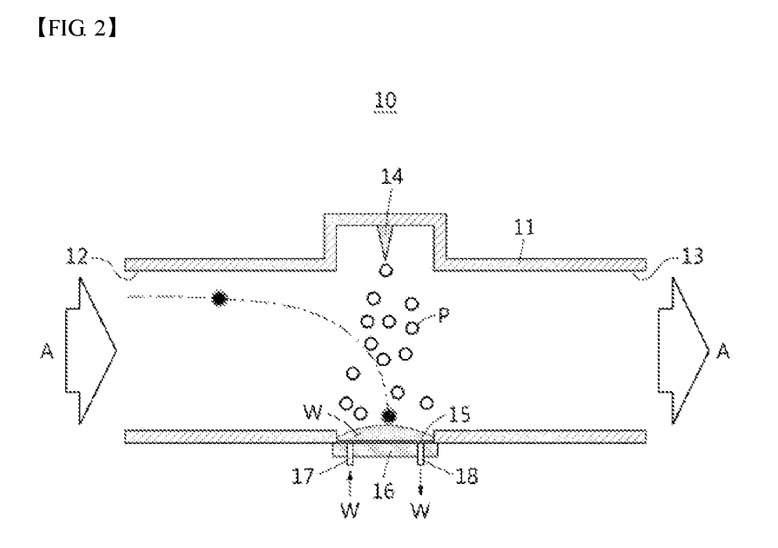
FIG. 2 is a block diagram schematically illustrating an embodiment of a capturer shown in FIG. 1.

As shown in FIG. 2, the capturer 10 electrically charges the air A including the particles P to be captured in the capture solution W. For this, the capturer 10 includes an inlet 12 into which the air A is introduced; a capture tube 11 formed to penetrate between the inlet 12 and an outlet 13 extending in a longitudinal direction from the inlet 12 to face the inlet 12; and first and second electrodes 14 and 15 disposed between the inlet 12 and outlet 13 of the capture tube 11 to face each other such that a high voltage can be applied to the first and second electrodes 14 and 15. Here, the first electrode 14 has a tip, and the second electrode 15 facing the first electrode 14 has a plate shape.

The first electrode 14 is a discharge electrode with a conductive metal that is formed at an end thereof, and the second electrode 15 is a plate-shaped ground electrode made of a conductive metal and disposed to be spaced by a predetermined distance from the first electrode 14. When a high direct current (DC) voltage is applied to the first electrode 14, corona discharge is generated at an end of the tip-shaped first electrode 14 so that the particles P in the introduced air A are positively charged.

The charged particles P in air A are captured in the capture solution W. Here, the capture solution W is introduced through a capture solution inlet 17 formed at the capture solution support 16, and then discharged through a capture solution outlet 18 formed thereat. For reference, it is exemplified that the capture solution W includes pure water (DI-Water) and the aerosol particles P including bacteria are captured in the capture solution W.

Meanwhile, it is exemplified in the present embodiment that the particles P in air A containing microorganisms such as bacteria are charged and captured in the capture solution W, but the present disclosure is not necessarily limited thereto. That is, a method of capturing the particles P in air A is not limited to the method shown in FIG. 2, and any one of various methods of capturing the particles P in air A into the liquid capture solution W may be used. For example, it is natural that the capturer 10 may be modified to adopt various capture manners such as electrostatic precipitation, an impinger, and a wet cyclone.

Here, bioaerosols captured in the capture solution W may include only a specific bioaerosol genus. In addition, a plurality of capture solutions W may be provided to different bioaerosol genera. Accordingly, a specific bioaerosol genus may be continuously introduced in real time by the particle sprayer 20. Here, the particle sprayer 20 will be described below.

Figure 3:
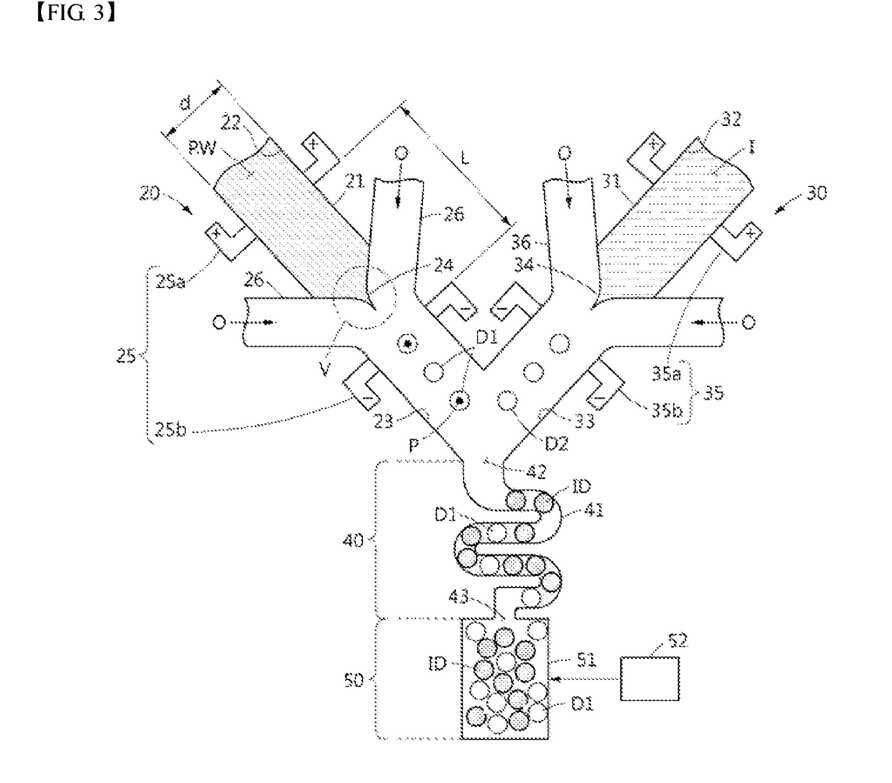
FIG. 3 is a block diagram schematically illustrating a particle sprayer, a reagent supplier, a reactor and an analyzer shown in FIG. 1.

The particle sprayer 20 electro-sprays the particles P captured in the capture solution W and individually discharges in the form of minute droplets D1 (hereinafter referred to as first droplets) containing a certain amount of the particles P. As shown in FIG. 3, the particle sprayer 20 includes a particle discharge body 21, a particle discharge cone 24, a particle controller 25 and a particle-specific oil supplier 26 and serves to spray the first droplets D1 including a certain amount of the particles P to a desired position at a desired speed.

The particle discharge body 21 is provided with a particle inlet 22 into which the particles P captured in the capture solution by the capturer 10 are introduced; and a particle outlet 23 configured to extend in a longitudinal direction from the particle inlet 22 and discharge the particles P to the reactor 40. The particles P captured in the capture solution W are introduced into the particle discharge body 21.

Figure 4:
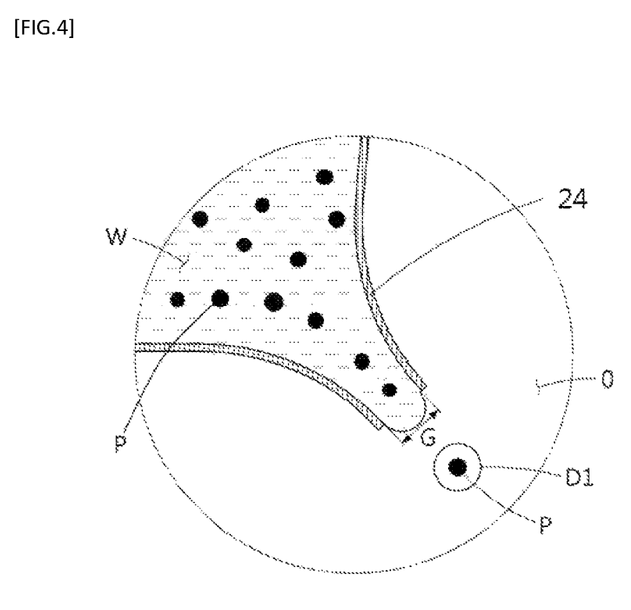
FIG. 4 is a schematically enlarged view of a V region of FIG. 3.

The particle discharge cone 24 is provided between the particle inlet 22 and the particle outlet 23 and has a Taylor cone shape to discharge the particles P captured in the capture solution W through the particle inlet 22 in the form of the individual first droplets D1. The cone-shaped end of the particle discharge cone 24 is a kind of nozzle, and is opened, as shown in FIG. 4, when an electrostatic force overcoming the surface tension is applied to electro-spray the particles P captured in the capture solution W in the form of the first droplets D1. Here, the size of the first droplets D1 to be electro-sprayed from the particle discharge cone 24 may be adjusted by controlling an open area G of the particle discharge cone 24.

The particle controller 25 controls an electrostatic force applied to the particle discharge cone 24 to control opening and closing of the particle discharge cone 24. The particle controller 25 includes a first positive electrode application body 25a for applying a voltage to a positive electrode and a first negative electrode application body 25b for applying a voltage to a negative electrode. The first positive and negative electrode application bodies 25a and 25b are provided on the particle discharge body 21, and the particle discharge cone 24 is provided between the first positive and negative electrode application bodies 25a and 25b. A voltage to be applied to first positive and negative electrode application bodies 35a and 35b is controlled by the particle controller 25. Accordingly, when electrostatic force generated by the particle controller 25 is controlled to be greater than the surface tension of the capture solution W in which the particles P are captured, the cone-shaped end of the particle discharge cone 24 is opened and the particles P captured in the capture solution W are electro-sprayed in the form of the first droplets D1.

Here, the open area G of the end of the particle discharge cone 24 may be controlled by adjusting an electrostatic force applied to the particle controller 25 as shown in FIG. 4, so that the size of the first droplets D1 electro-sprayed from the particle discharge cone 24 may be controlled. In addition, the particle controller 25 may control an inclination angle formed by the particle discharge cone 24, thereby controlling the size and discharge position of the first droplets D1 to be sprayed from the particle discharge cone 24.

For example, when the open area G of the particle discharge cone 24 is controlled to less than 1 μm by the particle controller 25, the particles P having a size of less than 1 μm are sprayed in the form of the first droplets D1 through the particle discharge cone 24. Here, since each of the first droplets D1 having a size of less than 1 μm discharged from the particle discharge cone 24 may contain only one particle P such as bacteria having a size of about 0.6 to 0.8 μm, each of the first droplets D1 electro-sprayed through the particle discharge cone 24 may contain only one particle P.

Accordingly, only the bioaerosol particles P, such as bacteria, having a size of less than 1 μm may be sprayed in the form of the first droplets D1 together with the capture solution W. Here, the first droplets D1 discharged through the particle discharge cone 24 may not include the particles P. That is, the first droplets D1 that have passed through the particle discharge cone 24 may not contain the microbial particles P and may be discharged in the form of pure water (DI water), i.e., the capture solution W.

Meanwhile, the size of the open area G of the particle discharge cone 24 controlled by the particle controller 25 is not limited to less than 1 μm and may be variously changed such that a certain amount of the particles P can be contained in the first droplets D1.

The particle-specific oil supplier 26 supplies the oil O to maintain the droplet state of the first droplets D1 discharged through the particle discharge cone 24. That is, the particle-specific oil supplier 26 supplies the oil O such that the shape of the first droplets D1 of the capture solution W wherein water is contained in the oil O is maintained like an emulsion wherein one of two liquids that do not dissolve each other is dispersed in the form of small particles on the other. The particle-specific oil supplier 26 supplies the oil O toward the end of the particle discharge cone 24 such that the oil O is directly supplied to the first droplets D1 sprayed from the particle discharge cone 24.

In the present embodiment, it is exemplified that a pair of particle-specific oil suppliers 26 are provided to face each other toward the end of the particle discharge cone 24 so as to supply the oil O, but the present disclosure is not necessarily limited thereto.

Meanwhile, it is exemplified that the first positive and negative electrode application bodies 25a and 25b of the particle sprayer 20 described in the present embodiment include an ITO electrode, and a spacing L between the first positive and negative electrode application bodies 25a and 25b is about 4 mm. In addition, it is exemplified that the diameter d of the particle inlet 22 is about 0.1 mm.

In addition, an application voltage required to discharge the first droplets D1 through the particle discharge cone 24 may be about 4000 V, and the following conditions may be applied to adjust the size of the first droplets D1 to 1 μm. That is, the capture solution W, in which the particles P introduced into the particle inlet 22 are captured, and the oil O may be supplied to the particle discharge body 21 in a ratio of a flow rate of the capture solution W:a flow rate of the oil O of 5 μL/hour:400 μL/hour, a voltage applied to the first positive and the negative electrode application bodies 25*a* and 25*b* may be about 6000 V, and the concentration of a surfactant such as Span 80 that may be contained in the oil O may be about 3 to 7%. Under such conditions, the particle discharge cone 24 may discharge the first droplets D1 having a size of 1 μm.

The reagent supplier 30 electro-sprays a reagent I, capable of reacting with the particles P, toward the first droplets D1 sprayed from the particle sprayer 20. The reagent supplier 30 includes a reagent discharge body 31, a reagent discharge cone 34, a reagent controller 35 and a reagent-specific oil supplier 36, similar to the particle sprayer 20.

For reference, it is exemplified that the reagent I described in the present disclosure includes a fluorescent liquid including luciferin/luciferase capable of fluorescently reacting to microorganisms in an ATP manner, but the present disclosure is not necessarily limited thereto.

The reagent discharge body 31 is provided with a reagent inlet 32 into which the reagent I is introduced; and a reagent outlet 33 configured to extend in a longitudinal direction from the reagent inlet 32 to discharge the reagent I into the reactor 40. Here, the reagent outlet 33 of the reagent discharge body 31 communicates with the particle outlet 23 of the particle discharge body 21, and the particle outlet 23 and the reagent outlet 33, which communicate with each other, of the first and second discharge bodies 31 and 41 are connected to the reactor 40. The reactor 40 will be described below. Accordingly, the particle outlet 23 and the reagent outlet 33 have a "Y" shape separated by two prongs with respect to the reactor 40.

The reagent discharge cone 34 is provided between the reagent inlet 32 and the reagent outlet 33 and has a Taylor cone shape to electro-spray the reagent I introduced through the reagent inlet 32 so as to discharge in the form of minute droplets (hereinafter referred to as second droplets D2) containing the reagent I.

The reagent controller 35 controls opening and closing of the reagent discharge cone 34 so as to control spray of the second droplets D2 containing the reagent I discharged through the reagent discharge cone 34. That is, the reagent controller 35 includes the second positive and negative electrode application bodies 35*a* and 35*b* to apply an electrostatic force greater than the surface tension of the reagent I, similar to the aforementioned particle controller 25. The second positive and negative electrode application bodies 35*a* and 35*b* are provided on the reagent discharge body 31, and the reagent discharge cone 34 is provided between the second positive and negative electrode application bodies 35*a* and 35*b*. The second positive and negative electrode application bodies 35*a* and 35*b* control electrostatic force generated by voltage application to be greater or smaller than the surface tension of the reagent I to open or close the reagent discharge cone 34.

Here, the reagent controller 35 controls the reagent discharge cone 34 to be opened to a size of less than 1 μm so as to electro-spray the reagent I in the form of the second droplets D2, similar to the particle controller 25. However, the present disclosure is not necessarily limited thereto, and it is natural that the opening area and conditions of the reagent discharge cone 34 may be variously changed.

The reagent-specific oil supplier 36 supplies the oil O to maintain the state of the second droplets D2 discharged through the reagent discharge cone 34. The reagent-specific oil supplier 36 supplies the oil O toward the end of the reagent discharge cone 34 to directly supply the oil O to the second droplets D2 sprayed from the reagent discharge cone 34, similar to the particle-specific oil supplier 26. In addition, it is illustrated and exemplified that a pair of reagent-specific oil suppliers 36 are provided to face each other toward the end of the reagent discharge cone 34 so as to supply the oil O, but the present disclosure is not necessarily limited thereto.

The particles P contained in the first droplets D1 and the reagent I contained in second D2, which are individually electro-sprayed through the particle sprayer 20 and the reagent supplier 30, are mixed and reacted in the reactor 40. The reactor 40 includes the reaction path 41 bent a plurality of times, as shown in FIG. 3. Here, the first and second droplets D1 and D2 are introduced through a mixing inlet 42 and mixed and reacted with each other via the reaction path 41, followed by being discharged to the analyzer 50 through a mixing outlet 43 connected to the reaction path 41.

For reference, the particles P among the first droplets D1 react with the second droplets D2 including the reagent I via the reaction path 41 to be stained in a state of reacted droplets ID. In addition, the first droplets D1 excluding the particles P do not react with the second droplets D2, thereby maintaining the state of the first droplets D1 as it is.

The analyzer 50 analyzes the particles P separated from the particle sprayer 20 by machine learning. More particularly, the analyzer 50 analyzes observed images of the reacted droplets ID, which are mixtures of the particle P-containing first droplets D1, among the first droplets D1 sprayed from the particle sprayer 20, and the reagent I-containing second droplets D2 mixed and stained in the reactor 40, by machine learning. Here, machine learning is an analysis method of providing improved information processing through learning using experiences of processing a large number of data, and the analyzer 50 learns and analyzes image data formed by continuously observing the particles P that have been continuously captured and have become minute droplets.

The analyzer 50 includes a collection container 51 in which the reacted droplets ID and the first droplets D1 discharged from the reactor 40 are collected; and a machine learning means 52 for analyzing the reacted droplets ID collected in the collection container 51, as shown in FIG. 3.

The collection container 51 communicates with a mixing outlet 53 of the reactor 40. In the collection container 51, the reacted droplets ID reacted with the reagent I to be stained; and the first droplets D1 excluding the particles P and thus unreacted with the reagent I are collected. In addition, the oil O discharged from the first and second oil suppliers 36 and 46 is also collected in the collection container 51.

The machine learning means 52 images the reacted droplets ID collected in the collection container 51 using at least one of equipment, such as a photosensor or a fluorescence microscope, allowing detection with the naked eye, and analyzes the detected image through machine learning. Here, the machine learning means 52 can analyze the appearance of microorganisms through imaging of the reacted droplets ID and analyze the analyzed appearance data through machine learning, which allows accurate classification of microorganisms.

For reference, in the present embodiment, it is exemplified that the reagent I includes luciferin/luciferase and, accordingly, the machine learning means 52 is a fluorescence microscope capable of photographing the particles P that fluorescently react with the reagent I.

Meanwhile, the machine learning means 52 machine-learns bioaerosols by genus and analyzes continuously introduced bioaerosols by genus using previously learned data. For example, when the capture solution W containing a first bioaerosol genus is introduced, the machine learning means 52 analyzes the concentration of the first bioaerosol genus by machine learning, and, when the capture solution W containing a second bioaerosol genus is introduced, the machine learning means 52 analyzes the concentration of the second bioaerosol genus in real time by machine learning. Accordingly, drawbacks of existing bioaerosol analysis methods by genus, such as a PCR detection method wherein it takes a long time and a sampling process is complicated, can be overcome.

Figure 5:
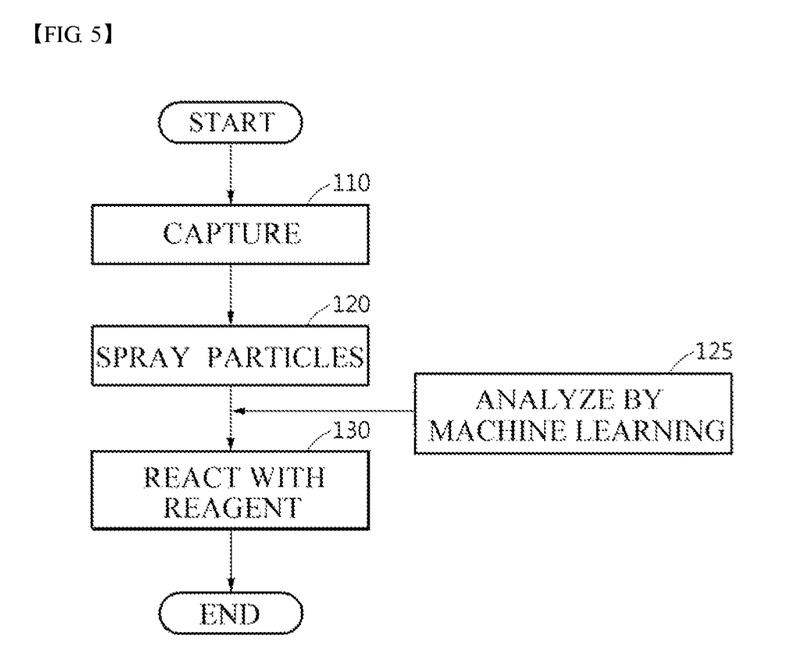
FIG. 5 is a flowchart schematically illustrating a method of monitoring bioaerosols according to a preferred embodiment of the present disclosure.

A method 100 of monitoring bioaerosols using the apparatus 1 for monitoring bioaerosols according to the present disclosure having the above configuration is described with reference to FIG. 5.

The method 100 of monitoring bioaerosols includes a capture step 110, a particle spray step 120 and a machine learning analysis step 130.

In the capture step 110, the bioaerosol particles P such as bacteria in air A are captured in the capture solution W. In the capture step, the particles P are captured in the capture solution W using corona discharge of electrically charging, as shown in FIG. 2. Here, it is preferred that the capture step 110 is continuously performed such that the air A is continuously introduced into and discharged from the capturer 10.

In the particle spray step 120, the particles P captured in the capture solution W are individually electro-sprayed in the form of the first droplets D1 to a constant position at a constant speed. In such a particle discharge step, the capture solution W including the particles P introduced into the particle discharge body 21 is electro-sprayed in the form of the first droplets D1 from the particle discharge cone 24 having a Taylor cone shape, as shown in FIGS. 3 and 4. Here, an electrostatic force applied to the particle discharge cone 24 is controlled by the particle controller 25, and the first droplets D1 are introduced to the reactor 40 side while maintaining the droplet shape thereof due to the oil O that is supplied from the particle-specific oil supplier 26 as soon as the first droplets D1 are discharged.

The first droplets D1 discharged from the particle spray step 120 may react with the reagent I in a reagent reaction step 125. In the reagent reaction step 125, an electrostatic force for applying the reagent I to the reagent discharge cone 34 having a Taylor cone shape is controlled by the reagent controller 35, so that the reagent I is electro-sprayed in the form of droplets such as the second droplets D2, as shown in FIG. 3. Here, the second droplets D2 are introduced the reactor 40 while maintaining the droplet shape thereof due to the oil O supplied from the reagent-specific oil supplier 36 as soon as the second droplets D2 are discharged.

For reference, the first droplets D1 in the particle spray step 120 and the second droplets D2 in the reagent reaction step 125 are simultaneously sprayed, thereby being introduced into the reactor 40 while maintaining the droplet shapes thereof due to the oil O. However, the present disclosure is not limited thereto, and the second droplets D2 in the reagent reaction step 125 may be sprayed after the particle spray step 120 or the first droplets D1 in the particle spray step 120 may be electro-sprayed after electro-spraying the second droplets D2 including the reagent I in the reagent reaction step 125.

In addition, in the reagent reaction step 125, the first and second droplets D1 and D2 are introduced into the reaction path 41 bent a plurality of times and mixed and reacted therein. Here, the first droplets D1 containing a certain amount of the particles P among the first droplets D1 react with the reagent I of the second droplets D2 to be stained in the form of the reacted droplets ID, and the first droplets D1 excluding the particles P only contain the capture solution W as a pure component and thus do not react with the second droplets D2, thereby maintaining the state of the first droplets D1.

In the machine learning analysis step 130, image data obtained by observing the reacted droplets ID is analyzed by machine learning. Here, the machine learning means 52 continuously photographs the continuously introduced reacted droplets ID in real time using a photographing means such as a fluorescence microscope and analyzes the obtained images by machine learning. Here, in the machine learning analysis step 130, the machine learning means 52 machine-learned with images of the reacted droplets ID analyzes concentration information on each bioaerosol genus in real time using the previously learned data.

Accordingly, the distribution, number, volume, etc. of the bioaerosol particles P contained in air A may be detected and monitored in real time. In addition, by analyzing the appearance of the bioaerosol particles P by machine learning, the particles P may be analyzed by genus, and measured data such as the concentration of each genus may be obtained.

For reference, introduction and discharge of the air A may be continuously performed in the capture step 110, thereby being capable of being continuously performed also in the particle spray step 120 and the machine learning analysis step 130. Accordingly, monitoring for each bioaerosol genus may be completely automated and it is possible to perform continuous measurement/analysis in real time.

In accordance with the present disclosure having the above configuration, first, the concentration of a specific bioaerosol genus among electro-sprayed bioaerosols can be detected through machine learning, so that monitoring efficiency for each bioaerosol genus can be improved.

Second, particles such as bacteria floating in air can be trapped by a certain amount in minute droplets, electro-sprayed to a certain position, and analyzed by machine learning, thereby enabling accurate appearance analysis and classification of microorganisms.

Third, continuous bioaerosol image processing through machine learning allows automation of bioaerosol monitoring and continuous measurement in real time. In addition, existing problems such as a long measurement time required for bioaerosol genus monitoring can be addressed.

While the present disclosure has been described referring to the preferred embodiments, those skilled in the art will appreciate that many modifications and changes can be

| [Description of Symbols] | |
|---|---|
| 1: apparatus for monitoring bioaerosols | 10: capturer |
| 20: particle sprayer | 21: particle discharge body |
| 24: particle discharge cone | 25: particle controller |
| 30: reagent supplier | 31: reagent discharge body |
| 34: reagent discharge cone | 35: reagent controller |
| 40: reactor | 50: machine learning analyzer |
| 52: machine learning means | P: particle |
| W: capture solution | D1: first droplet |
| D2: second droplet | ID: reacted droplet |

What is claimed is:

1. An apparatus for monitoring bioaerosols, comprising:
a capturer configured to capture bioaerosol particles in air in a capture solution;
a particle sprayer configured to electro-spray the capture solution in a form of droplets such that the particles are comprised in a certain amount in at least some of the droplets; and
an analyzer configured to analyze the particles, sprayed through the particle sprayer, by machine learning.

2. The apparatus according to claim 1, wherein the particle sprayer comprises:
a particle discharge body provided with a particle inlet into which the capture solution capturing the particles therein is introduced; and a particle outlet which extends in a longitudinal direction from the particle inlet and serves to discharge the droplets;
a particle discharge cone with a Taylor cone shape provided between the particle inlet and the particle outlet and configured to electro-spray the capture solution such that the droplets comprising a certain amount of the particles are individually discharged;
a particle controller configured to apply an electrostatic force greater than surface tension of the capture solution to the particle discharge cone so as to control opening and closing of the particle discharge cone; and
an oil supplier configured to supply an oil to the droplets discharged from the particle discharge cone so as to maintain a state of the droplets,
wherein the droplets are electro-sprayed to a constant position at a constant speed.

3. The apparatus according to claim 2, wherein an open area of the particle discharge cone is controlled by the particle controller such that the droplets contain a certain amount of the particles with a size of less than 1 μm.

4. The apparatus according to claim 2, wherein the capture solution and the oil are supplied in a flow rate ratio of 5 μL/hour:400 μL/hour to the particle discharge body,
a voltage of 5500 to 6500V is applied to a first positive electrode application body and a first negative electrode application body that respectively apply a positive electrode and a negative electrode, the particle discharge cone being disposed between the first positive electrode application body and the first negative electrode application body, and
the oil contains 3 to 7% of a surfactant.

5. The apparatus according to claim 1, further comprising:
a reagent supplier configured to supply a reagent, capable of reacting with the particles, toward the droplets discharged from the particle sprayer; and
a reactor in which the particles and the reagent are mixed and reacted, wherein the analyzer analyzes images, obtained by observing the particles reacted with the reagent discharged from the reactor, by machine learning.

6. The apparatus according to claim 5, wherein the reagent supplier comprises:
a second discharge body provided with a reagent inlet into which the reagent is introduced; and a reagent outlet formed to extend in a longitudinal direction from the reagent inlet and discharge the reagent;
a reagent discharge cone with a Taylor cone shape provided between the reagent inlet and the reagent outlet and configured to electro-spray the reagent; and
a reagent controller serving to control such that an electrostatic force greater than surface tension of the reagent is applied to the reagent discharge cone so as to control opening and closing of the reagent discharge cone.

7. The apparatus according to claim 6, wherein the reagent discharge cone sprays the reagent in a state of droplets, and supplies an oil to the reagent in a droplet state discharged from the reagent discharge cone to maintain the droplet state.

8. The apparatus according to claim 6, wherein an open area of the reagent discharge cone is controlled to a size of less than 1 μm by the reagent controller.

9. The apparatus according to claim 5, wherein the reactor is provided with a reaction path bent a plurality of times, wherein the droplets discharged from the particle sprayer and the reagent discharged from the reagent supplier are mixed in the reaction path.

10. The apparatus according to claim 5, wherein the reagent comprises a fluorescent liquid capable of reacting with microorganisms to stain the particles, and
the analyzer analyzes images, obtained by observing the stained particles using a photosensor or a fluorescence microscope, by machine learning.

11. A method of monitoring bioaerosols, the method comprising:
a particle spray process of electro-spraying a capture solution, in which bioaerosol particles are captured, in the form of particle droplets comprising a certain amount of the particles; and
a machine learning analysis process of observing the particles droplets to analyze the bioaerosols by genus through machine learning.

12. The method according to claim 11, further comprising a reagent reaction process of electro-spraying a reagent, capable of reacting with the particles, in a form of reagent droplets to react with the particles droplets,
wherein the machine learning analysis process comprising measuring and analyzing the particles droplets capable of reacting with the reagent.

13. The method according to claim 12, wherein the reagent reaction process comprising:
a reagent spray process of spraying the reagent in the form of reagent droplets; and
a reaction process of mixing and reacting the particles droplets with the reagent droplets,
wherein the particle spray process and the reagent spray process are simultaneously performed or the reagent spray process is performed before or after the particle spray process.

14. The method according to claim 11, wherein the particle spray process comprising:
a process of introducing the capture solution into a particle discharge body;

a process of electro-spraying the particles droplets comprising a certain amount of the particles from a particle discharge cone with a Taylor cone shape, provided inside the particle discharge body, to a constant position at a constant speed; and a first oil supply process of supplying an oil to the particles droplets, wherein an electrostatic force greater than surface tension of the capture solution is applied to the particle discharge cone so that opening of the particle discharge cone is controlled to spray the particles droplets.

15. The method according to claim 14, wherein an opening area of the particle discharge cone is controlled such that the particles having a size of less than 1 µm are comprised in a certain amount in the particles droplets.

16. The method according to claim 11, wherein the capture solution is continuously supplied in the particle spray process such that the machine learning analysis process is continuously performed in real time.

17. A method of monitoring bioaerosols, the method comprising:

a learning process of previously learning bioaerosols; and an analysis process of analyzing a capture solution, in which continuously introduced bioaerosols are captured, by machine learning, wherein the analysis process comprises monitoring the concentration of the bioaerosols by genus through the machine learning.

18. The method according to claim 17, wherein the capture solution is electro-sprayed in a form of droplets such that the bioaerosol particles are comprised in a certain amount and react with a reagent, and the analysis process comprises measuring and analyzing the particles droplets reacted with the reagent.

19. The method according to claim 17, wherein a plurality of capture solutions are provided to respectively comprise different bioaerosol genera, and the analysis process comprises respectively analyzing the plurality of capture solutions so as to analyze the bioaerosols by genus through machine learning.

* * * * *